United States Patent
Flickinger

(10) Patent No.: US 12,257,054 B2
(45) Date of Patent: *Mar. 25, 2025

(54) SYSTEMS AND METHODS FOR ESTIMATING AND PREDICTING EMOTIONAL STATES AND AFFECTS AND PROVIDING REAL TIME FEEDBACK

(71) Applicant: Gregory Charles Flickinger, Indialantic, FL (US)

(72) Inventor: Gregory Charles Flickinger, Indialantic, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/668,476

(22) Filed: May 20, 2024

(65) Prior Publication Data
US 2024/0315626 A1  Sep. 26, 2024

Related U.S. Application Data

(60) Continuation of application No. 17/470,247, filed on Sep. 9, 2021, now Pat. No. 11,986,300, which is a
(Continued)

(51) Int. Cl.
*A61B 5/16* (2006.01)
*A61B 5/00* (2006.01)
(Continued)

(52) U.S. Cl.
CPC .......... *A61B 5/165* (2013.01); *A61B 5/02055* (2013.01); *A61B 5/11* (2013.01);
(Continued)

(58) Field of Classification Search
CPC ....... A61B 5/165; A61B 5/02055; A61B 5/11; A61B 5/486; A61B 5/6803; A61B 5/681; A61B 5/6826; A61B 5/6898; A61B 5/7264; A61B 5/7282; A61B 5/742; A61B 5/021; A61B 5/024; A61B 5/0816; A61B 5/1116; A61B 5/112; A61B 5/14546; A61B 5/4266; A61B 5/4368; A61B 5/4393; A63F 13/212; A63F 13/25; A63F 13/33; A63F 2300/1012; A63F 2300/8082; A63B 24/0006; A63B 24/0062; A63B 24/0084; A63B 71/0622; A63B 2220/40;
(Continued)

(56) References Cited

U.S. PATENT DOCUMENTS 7,465,257 B1  12/2008  Morgan
9,412,233 B1   8/2016  Bagherzadeh
(Continued)

*Primary Examiner* — Robert J Utama
*Assistant Examiner* — Jeffrey K Wong
(74) *Attorney, Agent, or Firm* — OIPWC, LLC

(57) ABSTRACT

Systems and methods for estimating emotional states, moods, affects of an individual and providing feedback to the individual or others are disclosed. Systems and methods that provide real time detection and monitoring of physical aspects of an individual and/or aspects of the individual's activity and means of estimating that person's emotional state or affect and change to those are also disclosed. Real time feedback to the individual about the person's emotional change, change or potential change is provided to the user, helping the user cope, adjust or appropriately act on their emotions.

20 Claims, 11 Drawing Sheets

Related U.S. Application Data division of application No. 17/095,058, filed on Nov. 11, 2020, now Pat. No. 11,839,473, which is a continuation of application No. 15/632,313, filed on Jun. 24, 2017, now Pat. No. 10,835,168, which is a continuation-in-part of application No. 15/352,458, filed on Nov. 15, 2016, now abandoned.

(60) Provisional application No. 62/258,357, filed on Nov. 20, 2015.

(51) Int. Cl.

| | | |
|---|---|---|
| *A61B 5/0205* | (2006.01) | |
| *A61B 5/11* | (2006.01) | |
| *A63B 24/00* | (2006.01) | |
| *A63B 71/06* | (2006.01) | |
| *A63F 13/212* | (2014.01) | |
| *A63F 13/25* | (2014.01) | |
| *A63F 13/33* | (2014.01) | |
| *A61B 5/021* | (2006.01) | |
| *A61B 5/024* | (2006.01) | |
| *A61B 5/08* | (2006.01) | |
| *A61B 5/145* | (2006.01) | |

(52) U.S. Cl.
CPC ............ *A61B 5/486* (2013.01); *A61B 5/6803* (2013.01); *A61B 5/681* (2013.01); *A61B 5/6826* (2013.01); *A61B 5/6898* (2013.01); *A61B 5/7264* (2013.01); *A61B 5/7282* (2013.01); *A61B 5/742* (2013.01); *A63B 24/0006* (2013.01); *A63B 24/0062* (2013.01); *A63B 24/0084* (2013.01); *A63B 71/0622* (2013.01); *A63F 13/212* (2014.09); *A63F 13/25* (2014.09); *A63F 13/33* (2014.09); *A61B 5/021* (2013.01); *A61B 5/024* (2013.01); *A61B 5/0816* (2013.01); *A61B 5/1116* (2013.01); *A61B 5/112* (2013.01); *A61B 5/14546* (2013.01); *A61B 5/4266* (2013.01); *A61B 5/4368* (2013.01); *A61B 5/4393* (2013.01); *A61B 2503/10* (2013.01); *A63B 2220/12* (2013.01); *A63B 2220/40* (2013.01); *A63B 2220/56* (2013.01); *A63B 2220/803* (2013.01); *A63B 2220/807* (2013.01); *A63B 2220/808* (2013.01); *A63B 2220/836* (2013.01); *A63B 2225/50* (2013.01); *A63F 2300/1012* (2013.01); *A63F 2300/8082* (2013.01)

(58) Field of Classification Search
CPC .......... A63B 2220/56; A63B 2220/803; A63B 2220/807; A63B 2220/808; A63B 2220/836; A63B 2225/50
See application file for complete search history.

(56) References Cited

U.S. PATENT DOCUMENTS

| | | | |
|---|---|---|---|
| 11,986,300 B2* | 5/2024 | Flickinger | .......... A63B 24/0006 |
| 2004/0014566 A1 | 1/2004 | Kao | |
| 2007/0294089 A1 | 12/2007 | Garbow | |
| 2008/0318624 A1 | 12/2008 | Hedtke | |
| 2010/0062818 A1 | 3/2010 | Haughey | |
| 2015/0031964 A1 | 1/2015 | Bly | |
| 2015/0100141 A1 | 4/2015 | Hughes | |
| 2015/0187188 A1* | 7/2015 | Raskin | .............. H04M 1/72412 |
| | | | 340/407.1 |
| 2015/0201065 A1 | 7/2015 | Shim | |
| 2016/0042648 A1 | 2/2016 | Kothuri | |
| 2016/0066836 A1 | 3/2016 | Schneider | |
| 2016/0077547 A1 | 3/2016 | Aimone | |
| 2016/0157790 A1 | 6/2016 | Kleiss | |
| 2016/0228763 A1 | 8/2016 | Huang | |
| 2017/0021279 A1 | 1/2017 | Kim | |
| 2018/0035886 A1 | 2/2018 | Courtemanche | |
| 2018/0035938 A1 | 2/2018 | El Kaliouby | |
| 2018/0042540 A1 | 2/2018 | Kinnunen | |
| 2018/0049675 A1 | 2/2018 | Kerber | |
| 2018/0056132 A1 | 3/2018 | Foley | |
| 2018/0078850 A1 | 3/2018 | Klassen | |
| 2018/0116560 A1 | 5/2018 | Quinn | |

* cited by examiner

210

| INPUTS TO ALGORITHM - SIGNALS, SOURCES, DATUMS ||| 
| Sensors in wearables | SmartPhone | Physiological Sensors |
| --- | --- | --- |
| spectacles | Microphone | Skin chemicals |
| watch | camera | Subcutaneous vasculature |
| necklace | accelerometer | Pulse/bp/repiration |
| bracelet/anklet | gyroscope | temperature |
| ring | GPS | Pupil response |
| clothing | Pressure sensors | Muscle contractions |
| ear buds | Verbal/typing analysis | Hormone levels |
| Physio-halter | Voice analysis | perspiration |
| Body-electrodes | Facial analysis | |

DATABASE — 240 — PROCESSOR-ALGORITHM — 220
- user records, rules, tables
- Rules based engine
- database-lookup
- self learning-adaptive
- artificial intelligence - neural network

270

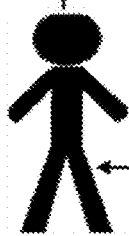

250

260

OUTPUTS OF ALGORITHM — 230
Estimated Emotional States
Relative Change of Emotional States
Ranking of Emotion States
Processed Personal Data
Maps of Emotions
Warnings, Feedback
Recommended - Actions
Therapy, Coaching

FIG. 2

| SIGNAL | WEIGHT | CHANGE | CHANGE RATE |
|---|---|---|---|
| Datum 1 | 20 | decreasing | - - |
| Datum 1 | 15 | decreasing | + |
| Datum 1 | 10 | constant | 0 |
| Datum 1 | 5 | increasing | ++ |
| Datum 1 | 30 | decreasing | ++++ |
| Datum 1 | 10 | constant | 0 |

FIG. 4A

| SIGNAL | WEIGHT | CHANGE | CHANGE RATE |
|---|---|---|---|
| Datum 1 | 20 | increasing | +++ |
| Datum 1 | 15 | increasing | ++ |
| Datum 1 | 10 | increasing | + |
| Datum 1 | 5 | constant | 0 |
| Datum 1 | 30 | increasing | ++++ |
| Datum 1 | 10 | constant | 0 |

FIG. 4B

SYSTEMS AND METHODS FOR ESTIMATING AND PREDICTING EMOTIONAL STATES AND AFFECTS AND PROVIDING REAL TIME FEEDBACK

RELATED APPLICATIONS

This application is a Continuation of application Ser. No. 17/470,247, filed Sep. 9, 2021, which is a Divisional of application Ser. No. 17/095,058, filed Nov. 11, 2020, now patent Ser. No. 11/839,473, which is a Continuation of application Ser. No. 15/632,313, filed Jun. 24, 2017, now U.S. Pat. No. 10,835,168, which is a Continuation-in-Part of application Ser. No. 15/352,458, filed Nov. 15, 2016, which originates and claims priority to U.S. Provisional Application No. 62/258,357, filed Nov. 20, 2015. All of the aforementioned applications are incorporated by reference herein in their entireties.

INCORPORATION BY REFERENCE

Except to the extent that any of the disclosure in the referenced patents conflicts with the disclosure herein, the following US patents and applications, which include inter alia disclosure pertaining to systems and methods of monitoring human physiological parameters, algorithms and artificial intelligence methods for multivariate computations and estimations, user feedback systems, virtual and computer based coaching, artificial intelligence and computer learning, and virtual reality systems and methods are incorporated herein by reference in their entireties: U.S. Pat. Nos. 9,039,614, 8,775,332, 8,509,882, 20150006192, 20130332160, 20140279800, 20130046151, 20110022332, 20110288379, 20090009284, U.S. Pat. Nos. 9,311,382, 9,552,739, 9,622,660, 5,870,768, 6,067,538, 7,065,512, 7,769,705, 20030101151, U.S. Pat. Nos. 9,215,996, 9,589,475, 9,630,093, 6,425,764, and 7,065,513.

FIELD OF THE INVENTION

Embodiments of the invention relate generally to systems and methods for predicting and estimating one or more emotional states of a person or changes thereto and providing feedback to that person or others.

BACKGROUND OF THE INVENTION

Smart phones and other devices incorporate a variety of transducers, sensors and other components for detecting, sensing, monitoring aspects of the world around them including such physical parameters as motion, location, acceleration, orientation, temperature, pressure, acoustical and optical waves, etc. These devices may also contain processing units capable, often in conjunction with software, to receive and potential store and analyze or otherwise process the information of the sensed physical world. In addition to smartphones, there are a growing number of "wearable devices" that can be incorporated into personal clothing other object possessed by individuals, e.g., in clothes, eyeglasses, watches, jewelry, bracelets, ear buds etc. and which may also detect, sense and/or record or transmit data about the world around them including data about the person onto which the wearable is fixed. An individual, with a smartphone and/or other wearable technology is able to detect and monitor aspects and inputs from and of the world around them, and with the onboard processor (or with a remote processor to which the data has been transmitted) can have that information filtered, processed and utilized to provide information to the user. Examples of such useful information being provided include the individual's location, the ambient pressure and temperature, the user motion during walking (e.g., pedometer), and the users sleep habits.

Humans are subject to emotions and emotional states throughout their lives and throughout each day; Emotional lability varies widely across personalities and circumstances, and emotions heavily influence behavior. Emotions can be very wide ranging and they are can have both positive and negative effects depending on the emotion, the circumstance, and how the individual who is experiencing the emotion, responds and/or perceives the emotion. For instance, the emotion of anger, if not recognized and checked can lead to a loss of temper and rage, which is many time regretted by the one losing their temper (not to mention those who receive the brunt of it). Similarly, the emotion of fear can cause one to flee from challenges resulting in failure.

Alternatively, the emotions of fear and anger can be channeled for positive purposes if recognized and directed to the appropriate ends. There is much literature, psychological and otherwise, written about how to deal with emotions, both positive and negative emotions and many people seek out means to identify, gauge, control, and channel their emotions in positive productive ways. Often, the difficulty in dealing with an emotion, whether positive or negative, is simply recognizing its developing presence. Cognitive therapy and other self-help habits, including positive feedback therapy, rely on recognizing what one is feeling as the first step in dealing with the emotion; once one know one is under the throes of a strong emotion such as fear or anger, one can use one's mind or other help to channel the emotion effectively and as the individual wants.

Mental emotional states can heavily influence actual behavior—in both positive and negative ways. Many times the key to success or optimal behaviour is self-awareness of oneself (know thyself)—moods or affect can be very powerful if used correctly—e.g., righteous anger resulting in assertiveness and courage to overcome or destructive if use wrongly e.g. fear causing worry, loss of confidence, failure. Example benefits of such a system include allowing one to recognize their fear, anger and other emotions in order to deal effectively and channel it properly and productively. Obviously there are many other emotions, including but not limited to, sadness, despair, joy, happiness, anxiety, etc., the detection, prediction of which and feedback to the user are contemplated by the invention.

Emotional stability and control are important to health, relationships and longevity. Understanding how one reacts under certain stressors and triggers as well as being able to proactively prepare, anticipate and channel emotions, including encouraging/enhancing positive/desired emotions and discouraging/reducing negative/unwanted emotions are examples of benefits offered by embodiments of the invention.

BRIEF SUMMARY

Embodiments of the invention includes methods of predicting an emotional state or affect of an individual and providing feedback to the individual comprising sensing, detecting or measuring one or more parameters of a person at a first time; sensing, detecting or measuring one or more of said parameters of the person at a second time; determining the changes or rates of changes to one or more of the said parameters between the first and second time; estimating an emotional state or changes to an emotional state of the person based on said changes or rates of changes of one or more of the parameters; and providing feedback of said estimated emotional state or changes to the emotional state of the person to the person.

In some embodiments parameters of a person include one or more of the group consisting of: physiological parameters; physical actions, verbal outputs both written or spoken, muscle tension, facial expression and sounds. In some embodiments physiological parameters of a person include one or more of the group consisting of: blood pressure, pulse, respiration, perspiration, skin salinity, temperature, subcutaneous vascular activity, pupillary response, bodily reflexes, blood chemistry including hormone levels, mandibular pressure, or physiological changes associated with sexual arousal. In some embodiments physical actions include one or more of the group consisting of: gesticulations or hand or arm motions, type and speed of gait, changes to head orientation such as head cocking or drooping, grip or finger pressure or fist clenching or changes thereto, body posture, speed or pressure used in manual activities or typing, speed and volume of articulation or sound enunciation such as yelling or whispering, weeping, smiling or laughing.

In some embodiments, the sensing, detecting or measuring is performed by the use of a smartphone wherein one or more of the hardware components integrated within said smartphone is used to sense, detect or measure a parameter of the person. In some embodiments the hardware components include one or more from the group consisting of: camera, microphone, accelerometer, gyroscope, thermometer, hygrometer, piezos and pressure sensors and GPS.

In some embodiments, a software application resident on said smartphone is used to receive data pertaining to said parameter from said hardware component at said first time and said second time, to determine a change or change rate to said parameter, to estimate an emotional state or change thereto of the person and to provide feedback to the person on an estimated emotional state or changes thereto of the person. In some embodiments, additional hardware components for sensing, detecting or measuring a parameter of a person are connected to said smartphone via either a direct physical connection or wirelessly. In some embodiments, the additional hardware is provided or included in one from the group consisting of: wearables, spectacles, temples, ear buds, scarves, necklaces, bracelets, watches, rings, skin patches, hats, halters, physiological monitors and other networked sensors. In some embodiments, a software application resident on said smartphone receives data pertaining to a parameter from a hardware component and transmits this data to a remote system, and wherein said remote system in wireless communication with said smartphone determines a change or change rate to said parameter and estimates an emotional state or change thereto and transmit this information to the smartphone which provides feedback to the person on an estimated emotional state or changes thereto of the person.

Other embodiments include a method of predicting or identifying an emotional state or affect of a first individual and providing a portion of that information to second individual comprising sensing, detecting, measuring or receiving one or more parameters of a first person at a first time; sensing, detecting, measuring or receiving one or more of said parameters of said first person at a second time; determining the changes or rates of changes to one or more of the said parameters between the first and second time; estimating an emotional state or changes to an emotional state of said first person based on said changes or rates of changes of one or more of the parameters; providing feedback of said estimated emotional state or changes thereto of the person to the person; and providing information pertaining to the estimated emotional state or changes thereto of said first portion to a second portion.

In some embodiments, a first person determines which information is provided to said second person, and the first person can adjust the amount and details of information to be shared with said second person through a software app or application. In some embodiments, the first person and said second person are remote from one another and exchange information including information on emotional states and changes thereto using smartphones, tablets, computers or other hardware using wireless communications and wherein such sharing of information may occur using social networking platforms.

In some embodiments, the estimation of an emotional state or changes to an emotional state are performed using a processor which relies on one or more methods of estimation or algorithms consisting of one or more of: rules based engine; database or lookup table; self learning adaptive system; neural network or artificial intelligence. In some embodiments, a person, by means of an software interface, may modify the methods of estimation or algorithm's inputs, weightings or baselines or other parameters in order to more finely tune said methods and algorithms and may provide other feedback including subjective feedback of said person's own emotional state in order to improve the accuracy of said estimations or improve an adaptive learning or artificial intelligence system used for estimating emotional states.

Still other embodiments include a system for predicting or identifying an emotional state or changes thereto of a person and providing feedback information to that person or another person comprising: one or more transducers for sensing, measuring or identifying parameters of a person during a time interval; a processor for determining the changes or rates of changes to one or more of the parameters over said time interval and for estimating an emotional state or changes to an emotional state of said person based on said changes or rates of changes of the parameters; and a user feedback means for providing feedback of said estimations by processor of emotional state or changes thereto of the person to the person. In some embodiments, at least one of said transducers and said processor and said user feedback means are incorporated in a smartphone. In other embodiments, at least one of the transducers is not incorporated into a smartphone and is a wearable or other device proximate to or in contact with the body of said person said transducer relaying data via wireless communication to a processor. In some embodiments at least a portion of the user feedback means is not incorporated into a smartphone and is proximate or in contact with the body of said person. In some embodiments, the system estimation of emotional states or changes thereto by said processor is accomplished using methods of estimation or algorithms consisting of one or more of: rules based engine; database or lookup table; self learning adaptive system; neural network or artificial intelligence. In some embodiments, the system comprises means for sharing the estimation of emotional states or changes thereto of one person to another person.

BRIEF DESCRIPTION OF THE DRAWINGS

FIG. 2 illustrates a system level diagram and process schematic according to some embodiments.

FIGS. 4*a-b* illustrate examples in tabular form of hypothetical measured and derived data used to estimate emotional state or changes to emotional states according to some embodiments.

DETAILED DESCRIPTION

Figure 1:
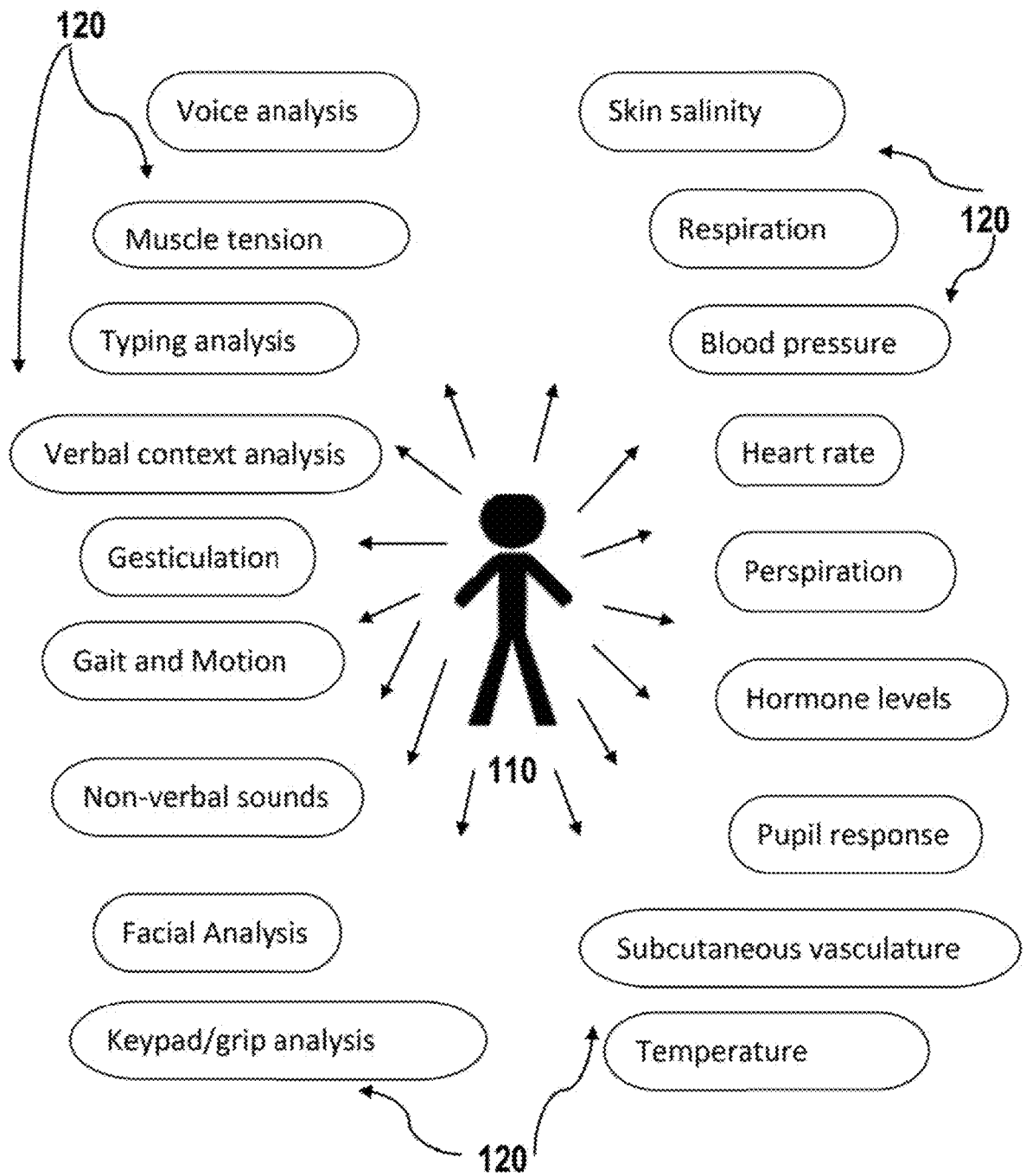
FIG. 1 illustrates a group of parameters associated with an individual that may be measured, received or generated and used to estimate emotional states or affects of the individual according to an embodiment.

Some embodiments of the invention are described in the following. In our fast paced and hectic world with many stimuli and psychological stressors, sometimes all at once, it is sometime easy for emotions such as frustration, anger, anxiety, worry, fear and others to develop or build up so rapidly that the individual is either unaware or "behind the curve" in recognizing these emotions and appropriately dealing with them. For example, some individuals may actually have trouble identifying their emotion correctly and/or knowing how to respond appropriate—e.g., to maximize the value of the emotion, avoiding hurting others or oneself, etc. Being able to recognize one's emotional state and also the change in one's emotions, e.g., the onset of anger or fear, to anticipate where one's emotional state is headed would be quite valuable to many in dealing with emotions proactively and positively. Moreover, having a real time feedback system that can forecast or predict emotional lability or other changes in emotion and/or provide helpful guidance in handling the emotion, e.g., instruction, encouragement, contacting of friend or medical personnel, would be a great benefit to many who may want to understand their emotional states, their "trigger buttons", and those who want to control and/or channel their emotions. For instance, one may wish to be alerted that they are moving emotionally towards anger so that they can take steps to prevent losing temper or saying the wrong things; or being alerted that one is becoming anxious in a social situation would allow the person more control and chance to be proactive because they understood what was going on. Furthermore, real time guidance or "coaching" helping one to deal with or channel the emotion the best way for the individual and setting would be beneficial to many. Some Embodiments of the inventions are directed at these goals of detecting affect or emotional states or changes (including in some embodiments of predicting or estimating of an individual's minute by minute emotional evolution), and providing real time feedback to the person on the state of their emotions/affect/mood and changes/evolution thereof—and in some embodiments real time guidance or other feedback that helps the user deal appropriately with their emotional state.

In one embodiment, and with reference to the drawings included herein the invention comprises a system that provides real time detection and monitoring of physical aspects of an individual and/or aspects of the individual's activity, determines, computes or estimates that person's emotional state or affect or estimates the change of, evolution too or increasing probability of a change in the individual's mood or emotional state occurring, and provides feedback, e.g., in real time, to the individual about the person's emotional change, change or potential change thereof. In some embodiments, the notification to user can take the form voice activated read-out, display on screen, vibration of device, watch or other wearable. In some embodiments, additional feedback is provided to the user, helping the user cope or appropriately act on their emotions and changes thereof. For instance, if the emotion of anger is identified, the user can hear a voice "calm down" or "anger ramping, be careful".

FIG. 1 illustrates an individual 110 and a group of associated parameters 120 of that individual that may be measured, sensed, detected or received via signals and/or datums and which may be further analyzed to estimate and emotional state affect, mood, the onset of such, or change thereto generally. These represented parameters are not an exhaustive list, but represent a subset of physiological and physical parameters or data as well as higher level derived analyses such as voice analysis, facial analysis, subcutaneous analysis, etc. According to some embodiments, by measuring and/or determining these parameters, or a subset of the parameters, in real time or in a near-continuous fashion, estimations of emotional states and changes to emotions are determined based on an estimating algorithm as further described herein.

FIG. 2 illustrates a system diagram according to some embodiments. Measured, detected, generated or received signals or datums are sources of input 210 to emotional predictive algorithm 220. These signals sources may be raw data or processed or filtered data or user entered data for example. Emotional predictive algorithm 220 produces Outputs 230 including but not limited to for example estimated emotional states or prediction of oncoming emotional states or transitions and one or more feedbacks to the user, for example, warnings, coaching, recommended actions etc. In some embodiments Algorithm 220 uses database 240 to retrieve baselining, benchmarking, rules, emotional look up information or other information, and may store processed data and predictions in database 240. User 250 is provided feedback 260 and may also, according to some embodiments, confirm or disconfirm feedback, adjust weighting to algorithm and provide other information 270 to tune algorithm.

Figure 3:
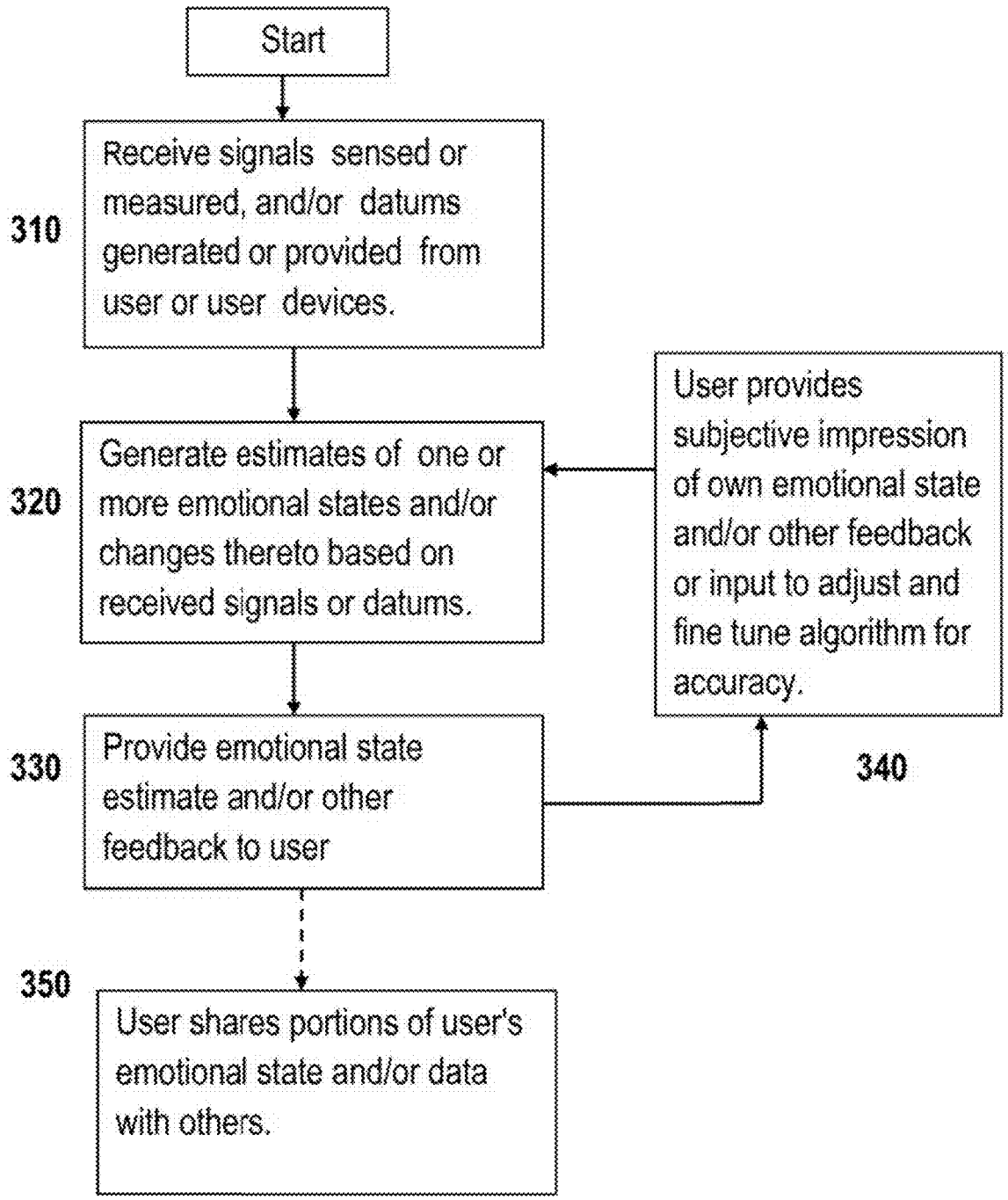
FIG. 3 illustrates the process flow of receiving signals or datums, estimating emotional states, and providing feedback according to some embodiments.

FIG. 3 illustrates the process flow of receiving signals or datums, estimating emotional states, and providing feedback according to some embodiments. Signals or datums generated by a person or devices or systems associated with a person are received 310. Based on received signals or datums, one or more estimates of the emotional state of the persons or changes to that person's emotional state are generated 320. One or more estimates or other feedback is provided to the person 320. In some embodiments, the person may provide feedback to the emotional estimating system 340 in order to more finely tune and improve the accuracy of the system. In some other embodiments, the person may share their emotional data or portions thereof with another person or party. This is an optional step and is shown as 350.

In one embodiment, the system is exemplified by an individual's smartphone; or tablet; these examples provide for mobile, real time and privacy protected data since the user is in possession of phone and the recording of data and processing of emotional data may reside on the user's phone or may be encrypted and communicated to/from a remote server or processor. In other embodiments a remote or local pc or other system receives data (e.g., from networked wearables), processes the data to generate an output of some mood or emotion related data and communicates this to user or other authorized party.

Example physical systems and "wearables" may include: smart phone, tablet, computers, smart glass type technology, smart watches, smart "tactical feedback" gloves, any type of wearable device or any combination of the aforementioned. Moreover these wearables can be controlled or be coordinated to operate as a system, e.g., in conjunction with a proximal or remote processor or using the processing capability of one or more of the wearables.

In one embodiment, measurements of one or more physiologic outputs and/or other idiosyncratic information particular to a user including but not limited to voice data, image data, muscle tension data, behavior etc. in real time and processing the data, e.g., with an algorithm, correlating the inputs and mapping inputs and correlated inputs to possible or likely emotional state, moods or changes of these, and reporting emotional related or indicative data (or raw data or data in whatever form desired) to the user.

FIGS. 4a-b illustrate in tabular form hypothetical measured data, changes to the data, and rates of changes of data used to estimate emotional state or changes to emotional state according to some embodiments. The column labeled SIGNAL contains specific datums. Datums represent specific input signals detected, measured or received by the affect prediction system and may be raw, pre-processed or processed signals and data representing a parameter of a person. Examples of datums include but are not limited to physiological parameters such as pulse, blood pressure, respiration, skin salinity, physical parameters, voice analysis including stress analysis, facial analysis, gesticulations or other motions (e.g., are measured by an accelerometer and/or gyroscope), muscle tension, keypad pressure or rates of typing, and direct user input and feedback. These datums and signals may be measured of generated as described elsewhere herein. In these examples, the column specifying WEIGHT represent weighting assigned to that particular datum or signal in estimating an emotional state or change and the weights are relative to other datums used in the estimation of affect or changes thereto. The column representing CHANGE represents the direction change (if any) of the signal/datum, for instance whether the signal/datum is increasing, decreasing or relatively constant. The CHANGE RATE column indicates that rate that the respective signal/ datum is changing (relative rate of change indicated by number of + signs; the greater number of + signs indicates a greater rate of change; 0 indicates a relatively constant value of the signal/datum or no change in that signal/datum.

FIG. 4a represents a hypothetical data set by which reduction in emotional tension is estimated. The reduction in specific datums (e.g., mandibular tension, respiration, and grip tension) with an increase in other datum (facial analysis showing a slight smile or less furrowed brow) provides the algorithm with an accurate estimation of emotional changes. FIG. 4b, another hypothetical example, illustrates changes and rates to specific signals/datum (e.g., teeth clenching, grip tension, typing pressure, and grunting sounds) indicating an incipient spike of anger.

Estimation of emotions experienced by a person, the intensity of such emotions and whether that emotion is increasing or decreasing may be accomplished by reference to a pre-populated database (e.g., a look-up table) that maps datums/signals, and their absolute and/or relative values to certain emotional states or meta-states. Alternatively a self-learning or adaptive algorithm with or without used input and feedback and fine tuning may be used to estimate emotional states or changes based on the measured signals/ datums.

Figure 5B:
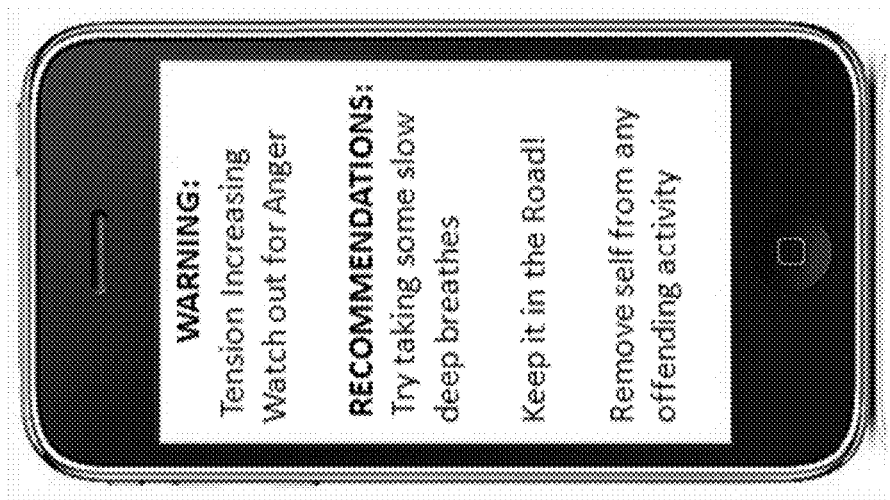
FIGS. 5*a-c* illustrate examples of feedback to the user according to some embodiments.
Figure 5A:
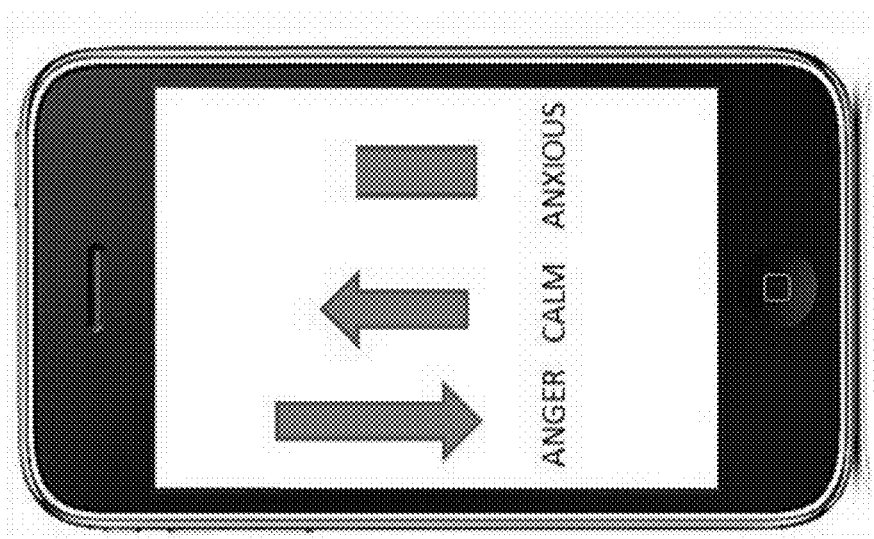
Figure 5C:
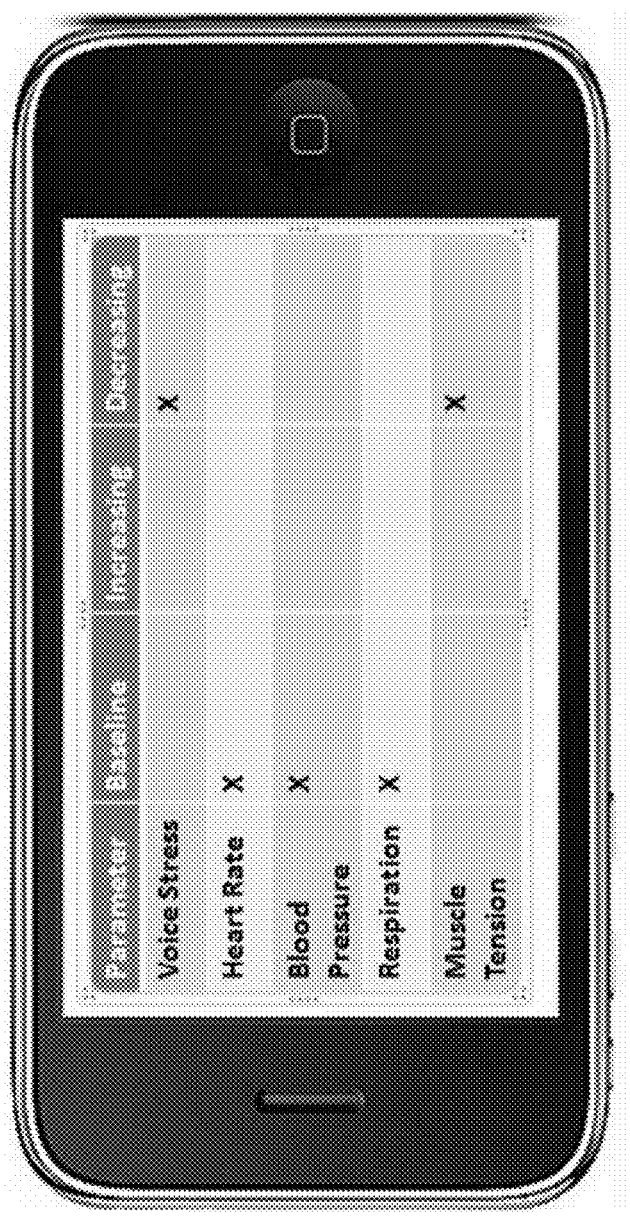

The feedback to the user may include coaching and/or recommendations of how to respond or what to do next. For example, in anger is sensed the system may say "calm down" "count to ten" or respond in a user programmed way, e.g., play favorite song. FIGS. 5a-c illustrate examples of feedback to the user of emotional state estimates according to some embodiments. In these hypothetical examples, FIG. 5a shows feedback to a user on their smartphone display regarding their emotional state and real time changes. In this example, three distinct emotive states are displayed (the actual display format and traits to be displayed may be set by user or application as desired according to some embodiments), the levels of anger, calmness and anxiety and their stability or lability as estimated by the emotional state estimation algorithm and system. In this example, the height of the bars represent the intensity of the emotion relative to a baseline and the arrows indicate whether that emotion is increasing or decreasing. In the present example, the level of anger relative to a baseline is still elevated but diminishing and the level of calmness is increasing; the level of anxiety is relatively stable. This can provide positive feedback to user and assist them in managing their emotions.

FIG. 5b illustrates and example of where the emotional estimating and feedback system warns an individual, via their smartphone display, of an increase in anger levels and coaches or recommends specific actions to deal or ameliorate any anger. FIG. 5C illustrates another way to display emotional feedback to a user on their smartphone. It is important to note that there are a variety of ways to provide feedback to a user, and such is not limited to a smartphone or other display. For example, a vibrating ring or bracelet, sounds via ear buds, heads up display, etc, may be used to provide feedback to the user and embodiments of the invention are not limited to any particular means of providing feedback.

Additional Examples Embodiments and Implementations

Although the following sections describe example embodiments and many different characteristics, traits, responses, and outputs of an individual user, it is to be understood that these are examples only and embodiments of the invention are not limited to what is described and furthermore do not need to include each and every feature described. For instance, a single data stream/point representing the user (e.g., voice analysis) may be all that is need in a certain application to accurately identify the desired information (e.g., stress or calm). Another embodiment may need 2 inputs; another may use a dozen, etc.). The attached drawings show some embodiments of the invention consistent with and inclusive of the disclosure herein.

In some embodiments an individual has smartphone (or other smart type device) and uses hardware and software (OS and apps) to effect and implement the emotional detection and feedback system. The hardware including sensors and other component chips may be incorporated in the smartphone and additionally may be added on via a hardware plug in (e.g., using the available ports/jacks on the smartphone itself or networked to phone (e.g., via bluetooth or other comm protocol). One or more apps on the smartphone (or may be remote on networked computer), reads real time data of sensors and other devices and estimates an emotion state or dominant state or changing emotions or states (e.g., increase in fear or anger) and provides real time feedback (and in some cases coaching) to user about at least one of: their current activity, physiologic state, emotional status, changes in emotional affect or the like.

The processing system uses a multivariate approach to estimate affect or changes thereto base on the multiple variables and changes that are present. The algorithm for estimate mood/affect/emotions may be based on a look up table where certain detected user measured or analyzed data is weighted and correlated to a likely emotional state. For example, if pulse increases and keypad typing pressure increases, this may indicate increasing anger, whereas if the pulse increases but the keypad pressure decreases may indicate increasing fear. The algorithm may be a self-learning and adapting system (e.g., neural network), and may get information from user (e.g., user inputs their self-perceived emotion state or user confirms or disconfirms algorithms estimate of emotional state); this baselining and input from the user can be used to finely tune the algorithm to provide more accurate and tailored results to the user.

The system provides feedback to user on their emotional state, and may provide feedback via numerous ways; for example a screen display showing likely emotions and changes thereto; an audio report or warning, a vibration warning or pattern of vibrations through the phone to represent emotions or warnings. The feedback may also be provide via non-phone hardware (ear buds, heads-up display on spectacle, pressure or squeezing from watch, etc.). Various ways of relating information to the user will be evident to one skilled in the art.

Examples of native phone hardware and associated user specific information that may be derived and used to infer emotional state may include (but not limited to):

accelerometers and gyroscopes—which can provide real time data on user's motion, acceleration, orientation, etc. This information may reveal changes in gesticulations, speed of reaction, pauses and the like, each of which can be used to infer (alone or together with other inputs) emotional states or changing emotions.

microphone—can record ambient sounds including environment, speech, grunts, sighs, etc. Voice analysis and voice analysis including stress analysis (implemented via app or via a networked server) can be used to infer emotional effect of changes thereto. Records, filters, amplifies and otherwise processes audio and other vibrations. Voice analysis may also include analysis of the words spoken, the tone and frequency content/intensity of the voice and changed in these to estimate emotional state.

camera-pictures or videos of user can reveal emotion states-via facial expression recognition for example email/text analysis-changes in use of words, typing and spelling/grammar mistakes, length of communication and changes thereto can reveal potential changes in affect.

Examples of non-native hardware that can be connected/networked to smartphone may include (but not limited to):

pressure sensors—to measure magnitude and real time changes of user's grip on device—and the pressure they apply to buttons, screen and keypads. A case surrounding the phone may have the sensors including a screen protector. [These sensors may also be built into the device itself (e.g., sensors integrated in case, keypad sensors—app to differentiate pressures, etc.).] By measuring changes to grip tension and keypad/button pressures when typing or clicking and changes in these variables, changes in emotional states (e.g., anger, anxiety) may be identified. (note: may be designed independently for keyboard wherein pressure on keys while typing—can be used by itself or with other indicators to identify affect and change in affect—allowing feedback to user—feedback can be positive (to encourage virtues such as bravery) or negative—to alert user to vice or loss of control or mistake such as with anger and fear.

Biometric and physiological sensors

Temperature, pressure, acoustic, optical sensors, chemical sensors in proximity to body can be used to measure of estimate user's physiologic characteristics, for example core or skin temperature may be measured with wearable or ear bud. Pulse rate with an acoustic sensor. Blood pressure with pressure sensor (e.g., arm band). Skin salinity with chemical sensor in watch or ring. Muscle tension including facial muscle and tempuromandibular tension with temples from glasses or headband. Respiration rate through a pressure or "tension" sensor incorporated in bra or shirt. Pupillary reaction via "smart glass" technology or via camera or videocam.

Such sensors can be incorporated in a variety of different device, e.g., to be used or worn by the use. Wearable devices that can incorporate sensors to detect physiologic signals may include (but are not limited to): spectacles and temples, headband, headphones, ear buds, necklace/pendant, bracelet/anklet, watch, clothing including shoes and belts, skin patches, rings, etc.

Benchmarking, Baselining, and Self-Learning System

Because different individuals may have difference emotional make-ups, e.g., some are more or less emotional labile that others, some are more or less prone to specific emotion, have different trigger points, have a harder or easier time recognizing and/or coping with a specific emotion, in some embodiments of the inventions, as baselining or benchmarking of each individual is performed in order to enhance, improve or optimize the system's ability to timely and accurately detect emotional status indicators and provide feedback to user. Additional baselining variables include idiosyncratic behavior of the individual. For example each individual may have one or multiple normal baseline and/or set of norms in their physiological responses (e.g., pulse, respiration, bp, skin salinity, pupillary response, muscle contraction etc.) physical gestures, voice, voice stress analysis, tones, words, typing habits, how tightly they hold a device etc. By measuring these variables, e.g., in a controlled condition such as relative calm, a baseline or norm for the user can be established. In some embodiments, user inputs known attributes about self or answers a questionnaire about self—the answers of which are used by the system to set thresholds and baselines. In some embodiments, the user monitors and adjusts the feedback received from the system to match the user own perception of their emotional state; this provides the system algorithm with additional data potential improving its performance by being tuned to the specific responses of individual user.

In some embodiments, real time measurement and analyses of one, several or all these inputs and variables is monitored to identify changes which may or are known to correlate with certain emotion states or states of mind, such as anger, impatience, fear or uncomfortableness, etc. The feedback system may include a means whereby the use confirms the accuracy of the system emotional diagnosis/reporting. In this example, the system is trained by the user, based on user feedback, input and/or confirmation by the user. In other example embodiments, the user may perceive an emotional state or change and provide direct feedback to the system and the system can associate the current measured data from that individual as indicative that emotional state. In some embodiments, the user can track their emotional states and changes over time and/or the user may deliberately insert themselves into a situation to trigger emotions, and monitor their emotional responses in real time via the system thereby providing a means of cognitive feedback therapy, In other embodiments, the system can be used to categorize personality types (e.g., analogous to Myers Briggs). By being exposed to certain questions, images, situations, and monitoring emotional changes, inference of personality type may be made.

Example Algorithms

The processing algorithm (or algorithms), which receives signal data that is generated by or associated with the user, and generates one or more outputs such as for example, compiled and processed raw data, estimated or predicted emotional state or states, identification of ramping up or down of certain emotions, changes and rates thereto, etc. may be implemented in a variety of ways as will be evident to one of ordinary skill in the art.

In some embodiments there may be a resident or remote database or server which stores raw data and/or historical and past data of the user and/or rules engine used to process input data and output emotional information. In some embodiments one or more look up tables may be employed; with a look up table, certain raw or preprocessed data are associated with one or more specific emotions or emotional responses (weightings and magnitudes and rates of change of the user signal data); the user data may be mapped in a multivariate way and the ordered and weighted input values at a given time may be compared to look up table for matching (or near matching) emotional state or changes thereto.

Other embodiments include a self learning algorithm that uses feedback from user to tune the algorithm for increased accuracy. For example, the user may initially set up a user baseline, e.g., user is particularly not easily upset or perturbed or conversely is very emotional labile and easily triggered into various emotional states. Or can specify certain emotions or physiological or physical responses associated therewith in advance to the system. The user may have access to "sliders" on screen in order to adjust the weighting to difference user inputs thereby adjusting the algorithm to give more or less weight (or ignore or focus solely etc) on any one or several of the user parameters or signals.

In other embodiments the system can use neural network or other adaptive multivariate systems to process the input data to estimate emotional state or affect. In some embodiments, the system outputs estimations of emotions and requests user feedback, e.g., for the user to input their own perceptions of their emotions, or to confirm, disconfirm or suggest modifications to the algorithms output; this allows for baselining a particular user, and fine tuning the algorithm for that particular user. Benchmark or other data, existing in the literature, e.g., psychology, behavior, medicine, psychiatry, etc. may be user to relate physiological states or changes (e.g., pulse, be respiration, skin salinity etc.)), physical activities (etc. muscle tension, key pressing, gesticulations, yelling, tearing, trembling, shivering, teeth clenching, etc) and other measured idiosyncratic data. Additionally or alternatively, user can input known "triggers" or stressors and known data about themselves in order to baseline and tune the algorithms.

Example Uses of the System

Although the following sections describe example uses and applications, it is to be understood that these are examples only of the potential uses and applications, and the uses or variations on implementation are not limited to what is described herein. A person of ordinary skill will recognize the wide applicability of a system as described herein and embodiments of the invention may include all useful application of the recognition and feedback system as exemplified herein. Providing monitoring, forecasting or predicting of emotional states or moods and/or changes thereof, alone or couple with a real time, near-real time or delayed reporting or feedback system has many potential applications. Without limitation and without being exhaustive, examples of uses include, but are not limited to the following examples Example uses of the systems and methods according to some embodiments include: Cognitive Therapy and Self Help and Awareness, and Positive Feedback and control. Be being aware of one's emotional states and lability in response to certain stimuli, one can cope or manage or even direct their emotional and actual responses in a positive way. By being aware of the triggers for both positive and negative emotions, one can seek to place themselves in positive situations and avoid negative ones. One can apply learned feedback techniques (e.g., anger or anxiety management) proactively with advance warning of the onset of an emotion. In general, one can learn to recognize and control or direct ones emotions in a positive way to improve themselves, their personality and their relationships and the system can provide one with increased control over one's feelings and behavior, and be a very empowering tool for self development. Cognitive Therapy (and other psychological therapies involving post mood analyses or real time feedback and control).

Personality Identification. Emotional data collected over time or in or in real time as response to specific psychological or physical stressors can be analyzed to predict certain personality traits, e.g., introvert or extrovert, analytical or feeling, etc.

Social Interaction. Learning about another, getting to know another more intimately, alerting the other to one's emotional state and emotional responses to the interaction (e.g., what the other person said or did) can allow individuals to more easily identify those who they would likely "click" with or develop a friendship as well as warn of incompatibility.

Feedback on advertising, products, political speech or anything else user is exposed to for which feedback of product provider is interested in—and this can be real time. In one embodiment, the user agrees to allow their emotional data (or portions thereof) to be share to provide of product/ad/speech, etc.

Group Input and Therapy—members of a group can selectively (or anonymously) share with members of the group (or other 3rd parties) their individual data and group collective data—like a focus group in one example—or in another case, to allow a group speaker to gauge the state of the group in order to tailor her speech appropriately.

Business/personal negotiations and presentation.

Sharing Data

In some embodiments, a user may want to share data in real time with another individual to allow them to appreciate the emotional affect of "the other"—mutual and/or reciprocal sharing would also be enabled. Embodiments include a sharing of emotional states between individuals, both in real time or non real time. In a real time sharing scenario example, 2 persons want to get to know each other and be aware of how they are making the other person feel and alert to any emotional changes in the other person to facilitate the communication or relationship (of course 1 person may share data while the other does not or they can share different types of data). In an embodiment, an app on a smartphone or tablet or PC would provide the real time emotional data of one party to the other. The details of what is shared could be controlled by the user providing the data. This allows for sharing of the "feelings" of the other person either in a face to face setting or where the individuals are separated (e.g., in different homes, office, countries). In another embodiment, voice analysis and/or voice stress analysis may be used as a means to communicate emotional status to the other party.

Exemplary embodiments include the ability of the user to keep his emotional responses data completely private and share only limited/filtered information to the extent he wishes with whom he so chooses. Other embodiments include multiple persons within groups sharing information with each other, or subgroups within, and a correlative function that identifies a "group emotion", a sort of weighting for the overall group composing the emotional responses of the members of the group.

In other embodiments, individuals can utilize certain "wearable" or other "connected" devices including headsets, armbands, etc, while chatting, texting or otherwise communicating with another person, for instance at their desk computer, and thereby share their emotional responses/state with the other person. This would facilitate "getting to know someone" remotely, and allows for a deeper appreciation of the other person's personality.

Other embodiments include non-real time feedback where the use or another entity (e.g., doctor) can review the time evolution of a user's emotion state (e.g, over the course of a day). The user can track their emotional changes to the events during the day and learn what triggers these changes, and thereby learn more about themselves, their emotional triggers (good and bad). For example, the output may be a daily chart/graph showing different emotional states and changes thereto throughout the day.

In some embodiments, the system, or components thereof, may be anonymous in some instances to facilitate privacy protecting collection of data for analysis. For instance, a user may wish to provide emotional feedback to an advertiser, but wants to remain anonymous. The privacy protected embodiment would allow the sharing of emotional data without identifying the individual.

In some embodiments, the system is implemented using a single "wearable" or other device attached or connect to users body providing real time sensing of one or more user variables allowing for an inference or estimation of one or more emotions, mood, affects, dispositions or inclinations. The signal processing can be accomplished on an internal processor of the device or in some embodiments by a remote processor connected to the attached device by wireline or wireless connections. In some embodiments the output estimation is conveyed directly to user or another party. Examples of such emotions/moods/dispositions include but are not limited to: anger. frustration, irritation, annoyance, impatience, intimidation, uncomfortableness, fear, worry, anxiety, calmness, relaxedness, ambivalence, surprise, astonishment, confusion, bewilderment, rage, warmth, sympathy, empathy, compassion, pity, attracted, aroused, love, desire, down, sad, depressed, loneliness, happiness, contentedness, joyful, excited, scared.

Some embodiments include an empathy trainer wherein individuals share emotional or other data and engage in real time meditation, dialog, therapy or other interaction that is at least in part driven by each individuals knowledge of their own personal data and/or that of the other person or persons (in the scenario of a group session). Such "sessions" with information sharing may facilitate bonding, personal and relationship growth among other things.

Additional Embodiments

Embodiments include methods and systems for providing an individual with estimates and analyses of their psychological state, makeup, inclinations, neuroses and other pathologies and the like. Embodiments include feedback to the user for helping guide the individual in understanding themselves, addressing any mood and/or psychological issues and generally helping the individual to improve themselves. Embodiments included automated and computer generated and directed coaching including psychological coaching, psychological diagnosis, and psychological therapies. Some embodiments include a virtual therapist for estimating a clinical psychological diagnosis based on input from a user or patient. In some embodiments, the virtual therapist provides coaching, counseling and/or forms of psychotherapy on a user or patient.

According to some embodiments, a virtual therapist may be implemented via an artificial intelligence (AI) engine and/or machine. Such AI machines are well known in the art, and may be programmed with information that in conjunction with self learning, can inter alia draw conclusions, make judgments, provide recommendations, direct activity etc. Such an AI engine may be implemented on a smartphone, tablet, and personal computer for example. In some embodiments, the AI machine is programmed with psychological diagnostic criteria and information as well as clinical therapeutic approaches, for example, similar to the diagnostic information and therapeutic techniques that are learned by trained therapists and psychologist. For example, the Diagnostic and Statistical Manual, the benchmark diagnostic tool and pathology manual of the psychological profession may be programmed (or read) by the AI machine (other diagnostic information and psychological assessment information) may also be read, learned or programmed into the AI engine). There are many standard psychological techniques and procedure for treatments and therapy as well that have been codified and systematized to some extent. Such information would be programmed or otherwise learned by the AI engine. Psychological diagnosis and therapy can be subjective to some extent and a wide variety of therapies are potentially available to treat pathologies or disorder. Such varieties of therapeutic approaches may be learned or programmed into the AI engine.

In some embodiments, the AI engine implemented systems and methods would comprise both diagnostic and therapeutic capabilities, including methods of diagnosing (or otherwise estimating one or more psychological parameters or state) of a patient or user, and methods for treating or counseling the patient or user. Methods for diagnosing and eliciting diagnostic criteria may include verbal responses by the user to questions originated by the AI engine, physiological states, and changes thereto, or other non-verbal responses from the user in reacting to local stimulus and/or that provided by the AI engine. In some embodiments, the virtual psychotherapist is resident on a personal computer and interfaces with user via a video camera and display, microphone and speaker, and various other sensor associated with the user or activities thereof. Non-verbal responses may include but are not limited to facial expressions, sounds, body postures orientation, muscle tension, idiosyncratic activity, body language, physiological data as measured by sensors (see FIG. 1 for example), and generally any measured or sensed input or reaction from the user that would assist in the diagnoses or in advancing the diagnostic process. The diagnostic process may be iterative wherein the AI engine queries and/or otherwise stimulated the user, receives one or more responses from the user, and further queries stimulated the user in accordance with the previously learned diagnostic criteria and diagnostic process. Once a diagnosis has been made or estimated, coaching of or recommendations to the user may be provided.

Psychotherapy by the AI engine virtual therapists may also be implemented at the user request using the learned therapies and therapeutics. Therapies may include any of the wide variety of known psychotherapeutic techniques and which have been programmed or learned by the AI engine. Examples of such include but are not limited to cognitive therapies. In cognitive therapy, the virtual therapists through the AI engine would engage in dialog with the user or human actor and implement therapy similar to how a human therapist would. Some therapies involve physical or other stimulus (including emotional stimulus via words, pictures, thoughts, etc). The AI engine would control actuators that would effect any necessary stimulus as part of the therapy.

In some embodiments, virtual reality (VR) is employed to effect the needed stimulus. For instance, the technique of "flooding" an individual with a known fear is a therapy to overcome that fear. As an example, and in no way limiting the scope of the invention, the AI virtual therapist determines that the user suffers from acrophobia or has a recurrent fear of falling from a great height that is manifested in the user's dreams. Using a VR mask or goggles, the user can be flooded with the experience of falling from great heights with the intent to sensitize the user from the fear that they have been experiencing. As described elsewhere herein, the user may employ wearable technology and this technology can be used as both a diagnostic aid (sensing data about the user) as well as a therapeutic aid (sending stimuli to the use and/or measuring responses to said stimuli).

According to some embodiments, VR may be used for baselining, testing, diagnosing, treating and coaching. Simulating environments, situations, human interactions as well as other stimuli via VR and other technologies, and receiving and analyzing feedback (verbal and non-verbal) from a user allows for diagnosing and treating psychological and personality conditions. The AI engine-virtual therapist may use algorithmic approaches to testing, diagnoses and treatment, based on for example, the standard practices psychology as programmed into and learned by the AI engine. Just as a therapist would dialog with a patient or user to uncover or elucidate personality traits and disorders, and apply iterative therapy to treat any disorder, the AI-virtual therapist would dialog with the patient or user (for instance analogous to a Turing machine), learn from the patient and apply the professional knowledge and learned skill of the psychological profession. Such dialog could occur via various ways, including for instance via a computer interface that includes a display and speaker by which the AI-therapist would communicate visually and audibly to the patient. If the patient was interface with sensors or actuators, the AI-therapist would be able to read and correlate these sensors in real time, and activate or engage any actuators (e.g., stimulus).

In one embodiment, the user interface with and to the virtual coach or therapist is implemented via a smartphone (in other embodiments, a personal computer or tablet). In some embodiments, the AI engine is resident on the smartphone. In other embodiments, the AI engine is remote from the smartphone (for instance, located on a computer with high processing capability). In some embodiments, diagnostic and treatments methods are categorized and stored in a computer data store (e.g., database) which is accessible by the AI engine to consult and continue learning.

Such AI driven psychological diagnostic estimation systems and methods, and particularly when implement on, at least partially (for instance a back end remote serve may comprise the stored data, encyclopedia diagnostic data act), a common computation device such as a smartphone or personal computer would have wide applicability. Potential applications include a personal assistant or psychological coach, implemented as an AI engine, that used known science of psychology and therapy, and help a person understand themselves more deeply and identify any perceived shortcomings or "pathologies" in their personalities (which they may want to improve), and help them eliminate or mitigate such personality or psychological disorders thereby improving themselves. Other applications include a virtual clinical psychologist that may be helpful where there is a shortage of human practitioners. The virtual AI driven diagnostician may be used by clinicians and others to pre-assess and/or triage patients or clients and thus provide enhance efficiency. The virtual tool may also be used as a clinician's aid in diagnosis and treatment. These are only examples of the applications, and embodiments of the invention are not limited to these.

Figure 6A:
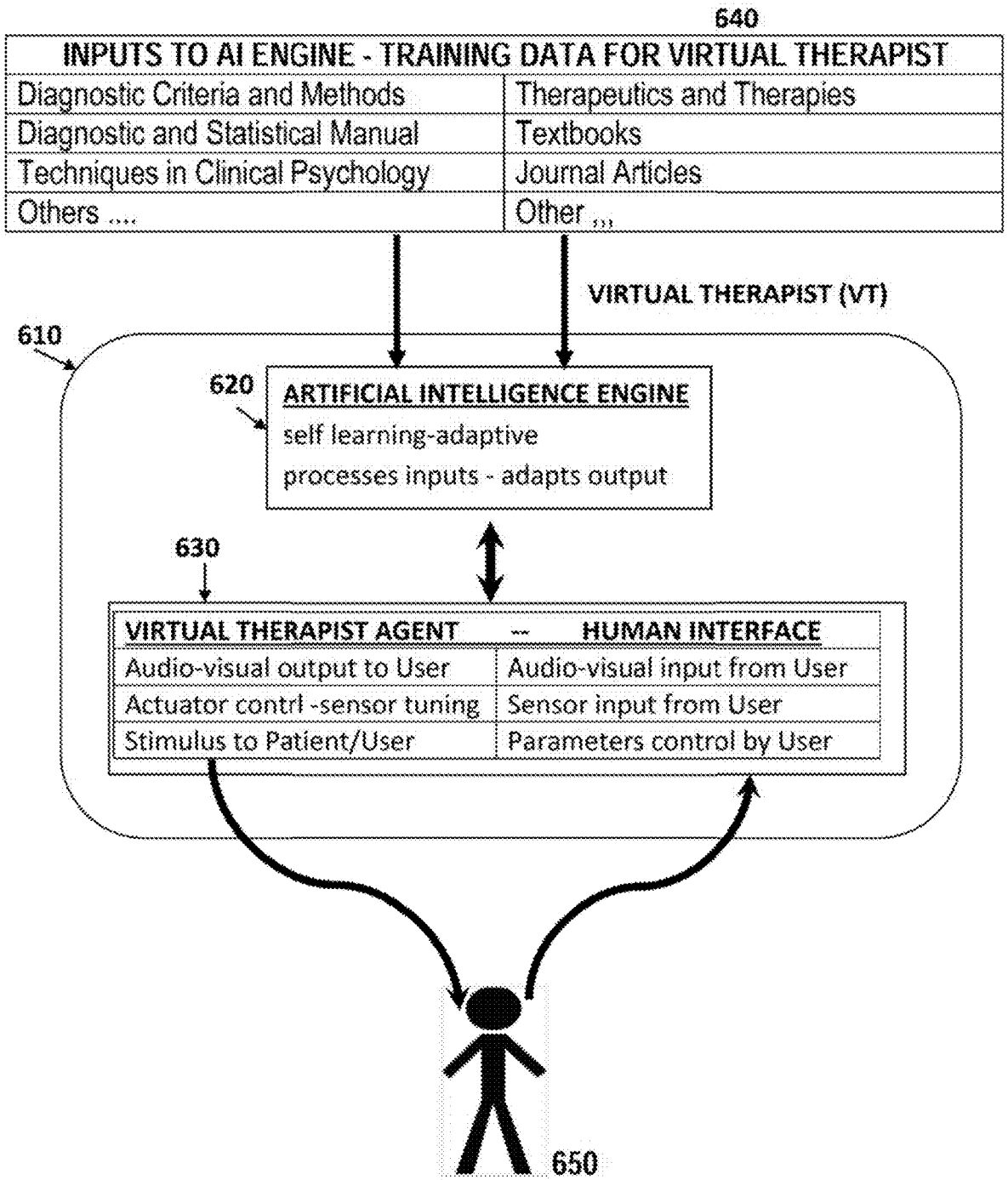
FIG. 6*a* shows a diagrammatical representation of the virtual personality coach or virtual therapists according to some embodiments.

FIG. 6a shows a diagrammatical representation of the virtual personality coach or virtual therapists according to some embodiments. Virtual Therapist 610 comprises an Artificial Intelligence self learning adaptive engine 620 and a Virtual Agent 630 comprising one or more human interfaces. The AI Engine 620 is programmed or otherwise loaded or primed with scientific knowledge, data and techniques comprising diagnostic and/or therapeutic standards and psychological expertise. The Inputs to the AI Engine 640 may be varied but in preferred embodiments include encyclopedic level of professional knowledge on diagnoses and treatment of psychological, personality and other disorders or pathologies of the mind and/or mood. The Virtual Therapist interacts with a user or patient 650 via the VT Agent 630. The VT Agent is controlled by the AI Engine 620, according to some embodiments wherein the AI Engine 620 receives user/patient input via the VT Agent 630 and directs output to the user/patient through the VT Agent 630. The Virtual Therapist 610 interfaces with the patient 650 via the Virtual Agent 630 and may engage in dialog with patient 650 via a microphone and speaker, may record the patient's movements, expressions, body language etc with video cameras, motion sensors and other sensors attached to the patient's body or chair and by other means. The patient 650 may be equipped with biological sensors or detectors which provide data to the VT 610. The VT 610 may initiate stimulus on the patient 650 through the Virtual Agent 630. In some embodiments, virtual reality, e.g., in the form of conventional VR goggles are used to apply stimulus and/or sense patient response. By iterative dialog with, stimulus of and reception of measurement of patient actions, responses and states (e.g., via physiological and other sensors), the Virtual Therapist 610 can effect psychological diagnoses and/or therapies similar and analogous to how a human therapist would interact, diagnose and treat a patient. In some embodiments, the Virtual Agent 630 is resident on an individual's smart phone or personal computer, and dialog, stimulus and user response/data is input through this device. In some embodiments, the AI Engine 620 is co-located on a user's device. In other embodiments, the AI Engine 620 is located remotely on another computer and communicates wirelessly with the Virtual Therapist 630 resident on the user's device.

In some embodiments, the AI Engine 620 is preprogrammed with an extensive amount diagnostic, therapeutic and other professional and scientific knowledge (for instance the DSM and Clinical Treatment manuals, monographs, etc). In other embodiments, the AI Engine 620 is programmed with a basic amount of knowledge and has accesses to separately stored knowledge based, and accesses such data stores to enhance the AI Engine's learning and knowledge or in response to a specific therapy or coaching session.

Figure 6B:
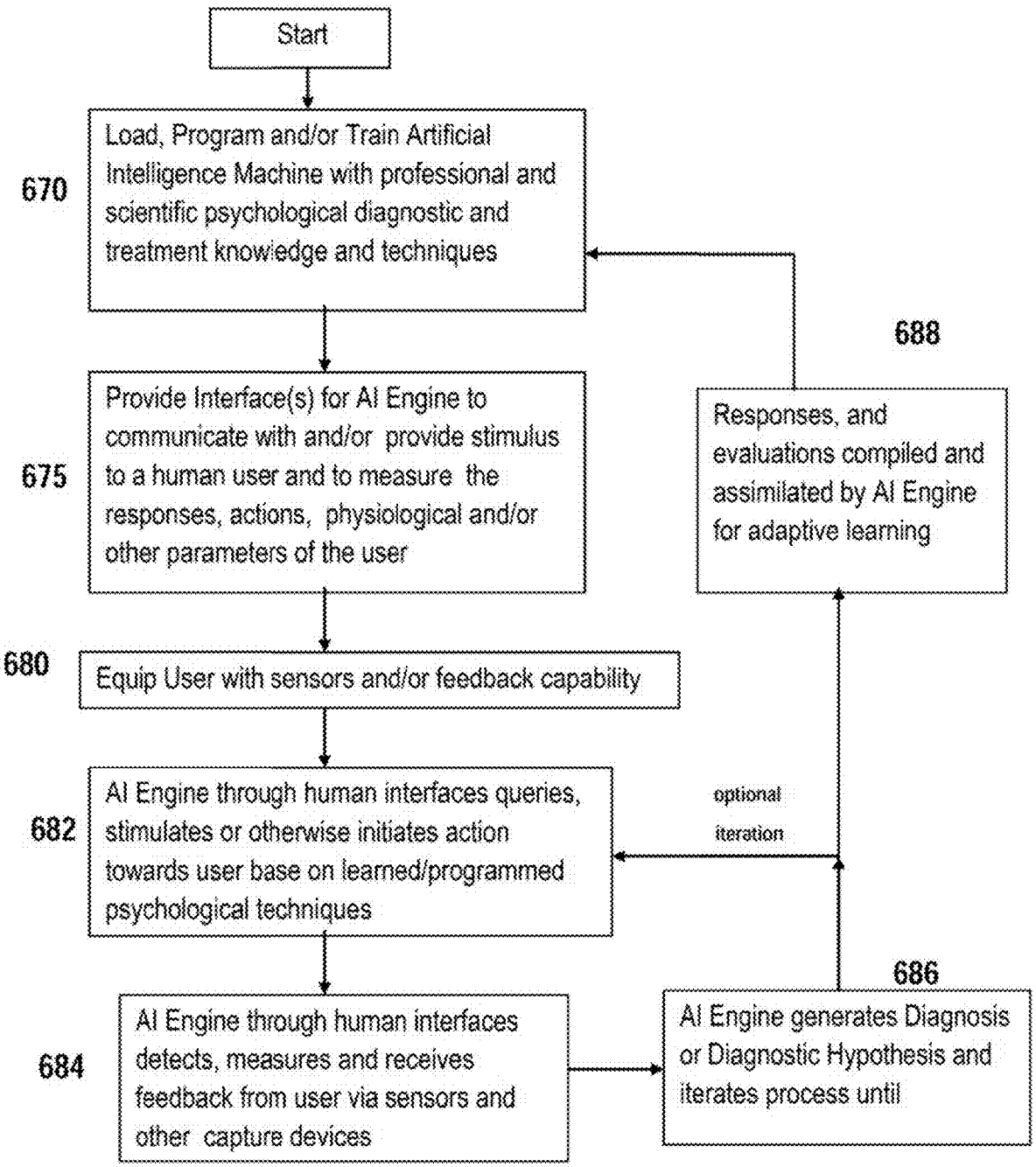
FIGS. 6*b-c* show process flows of the implementation of diagnostic and treatment processes of virtual therapists according to some embodiments.
Figure 6C:
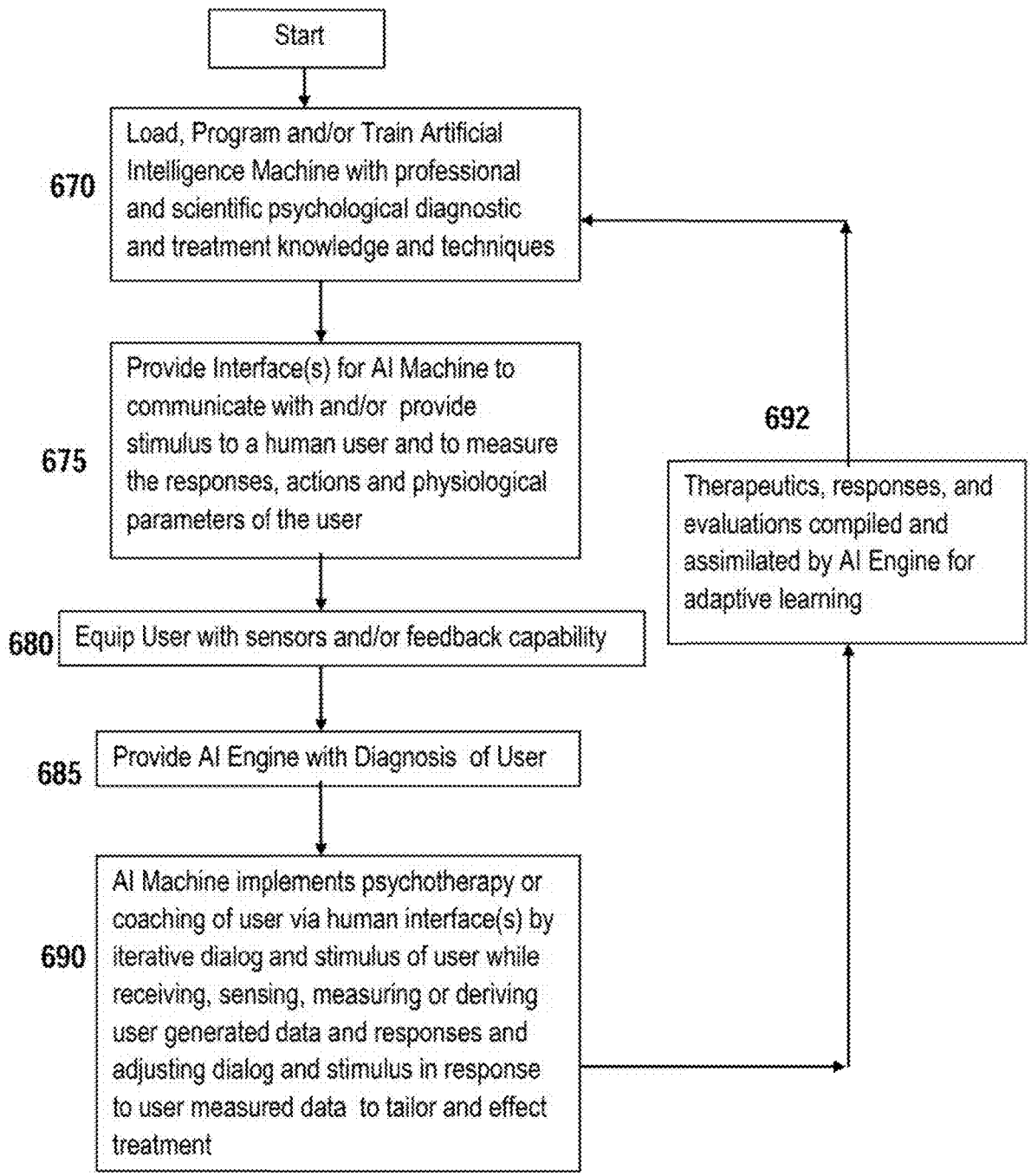

FIGS. 6b-c show process flows of the implementation of diagnostic and treatment processes of virtual therapists according to some embodiments.

Personal Data Sharing

According to some additional embodiments of the invention, users share personal data in real time, data including but not limited to physiological, physical and other raw data and/or derived data such as estimation of moods or estimations or changes thereto. One example application is in the field of computer gaming which is a vast and diverse global industry and recreational pursuits. Individuals routinely play games where they are remote from one another, but are connected to a game via the Internet or other communication means. Because the users are connected via communication links, they can play and enjoy gaming as if they are together. According to some embodiments, gaming may include sharing one or more of a user's personal data with other users and/or sharing it and having the data become part of or an objective or target of the game itself.

In one embodiment, users are playing an identical game, and one user is performing better than another; the higher performing user's data may be shared with the lower performing user such that the latter can potentially adjust his data (e.g., via coaching or simple observation) to more align with the former thus improving performance. In some embodiments, user data is integrated into the scoring system of the game and players compete, at least in part, by trying to optimize or control their personal data (e.g., control their fear, improve their concentration, etc.) In some embodiments, users may share only a portion of their data and only for a certain time period; users can "buy" data using game credits according to some embodiments. All these features may facilitate enjoyment, competition and learning in the gaming environment.

In some embodiments, the game itself may be designed around or scored according to a user's personal data (for example, minimizing/maximizing heart rate, sweat, muscle tension, facial expressions, etc). Additional parameters of game performance may be derived parameters such as user's emotional state (fear, anger, fatigue, etc). Embodiments of the invention include computer gaming that has as its object, goals, targets, or metrics, real time generated personal data (raw or derived) of a player (such data includes those as shown in FIGS. 1 and 2. Embodiments also include sharing player data with other players (e.g., via gaming console, heads up display, VR goggles, etc). Such gaming can be implemented via various convention means as will be evident to those skilled in the art. As described elsewhere herein, a user or player may be connected to one or more sensors that read raw data and an affect estimator that that estimate moods and emotions, and this data or a subset thereof may be used by the game to add complexity and enjoyment to the game. Such gaming and scoring involving certain raw or derived user data may be used also when the user plays against the computer itself (that is, some embodiments of gaming using user data as part of the game algorithm and/or scoring are solitary and do not involve another individual playing in real time).

Figure 7:
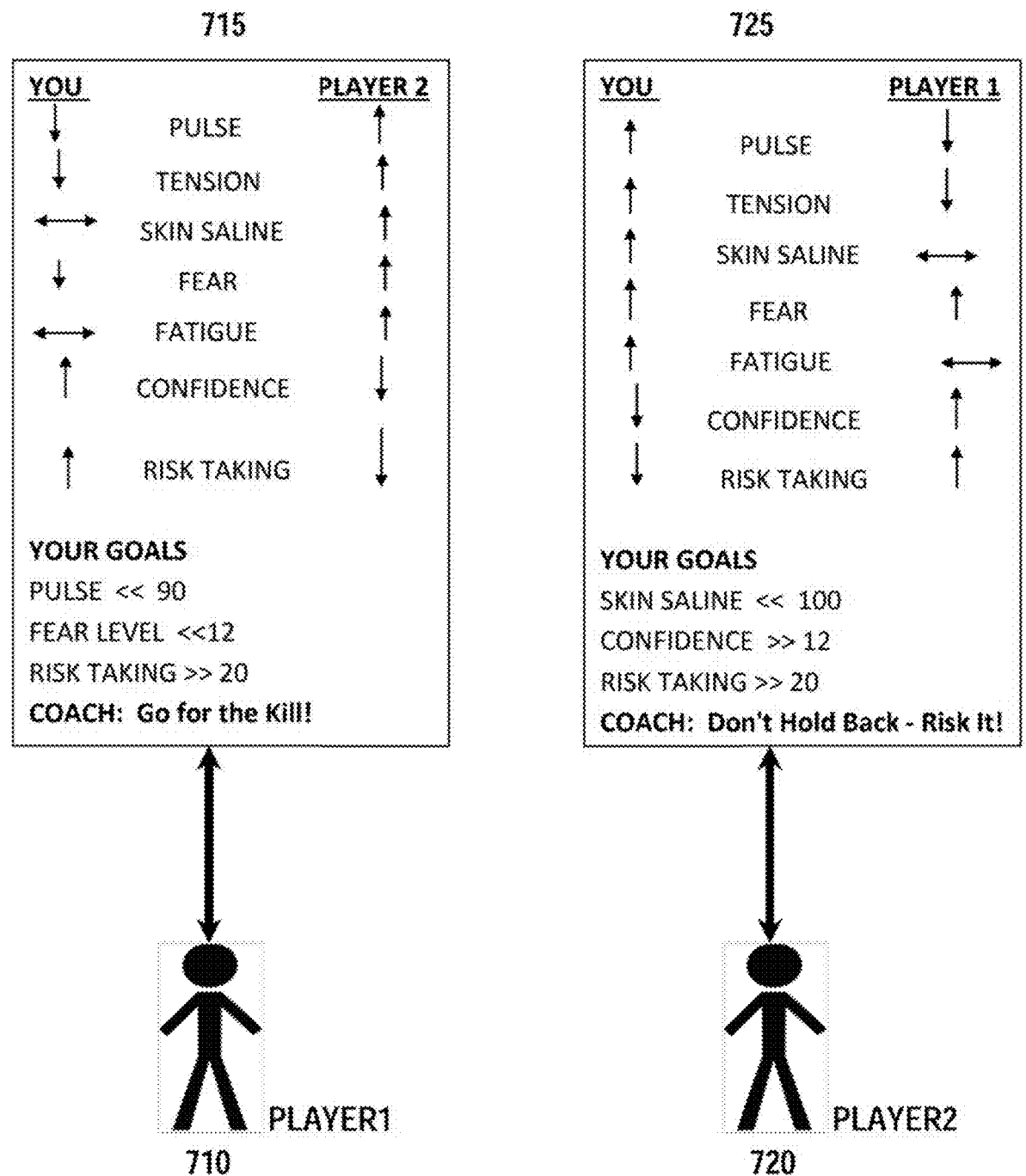
FIG. 7 illustrates an example gaming interface and display according to some embodiments.

FIG. 7 illustrates an example gaming interface and display according to some embodiments. While the details of the specific game and game interface are not shown, as gaming and user interfaces are well known in the art, what is shown according to embodiments of the invention are the real time display of players personal data. Player1 710 and Player2 720 are equipped or fitted with biological and other sensors (not shown) which measure in real time physiological and other player data. The sensors data and derived data constitute inputs into the game display, game algorithm or both. In some embodiments the local processor analyzes the data to generate an estimated emotional state or affect for display to the player. The data collection for and on each player is synchronized with that of other players and the raw and derived data is displayed on game console/display of each player. Player1 display 715 and Player2 display 725 shows gamer raw and derived data, including data for both Player1 710 and Player2 720. The players see their own user data and the data of one or more other gamers. For example, the data measured and displayed for this game include raw data of pulse, tension and skin responses, and derived data relating to estimated fear, anxiety and confidence. These data may be used by one player in competition with another player and may form metrics, objective or milestones of the game itself (e.g., score points for achieving, changing or eliciting specific player data, either one's own or that of another player). The displays 715 and 725 may also show a variety of other gaming attributes, but these are not shown for the sake of clarity.

In some embodiments, one or more datums associated with a first individual or entity, including for example, physiological data, physical or motion data or any other derived data associated with a user including estimated emotional affect or changes thereto, is shared with a second individual or entity. For example, when engaging in a sporting activity or physical fitness training, information and data from one person may be voluntarily shared with person or persons. The person who receives the data may communicate back to the originator of the data, for example in the form of coaching or other types of feedback. In some embodiments, individuals mutually share their data or portions thereof, for example in real time. This may facilitate training together and mutual motivation and learning. Because the sharing of information may be accomplished via wireless or other communications, the individuals sharing data may be remote to one another (across town or around the world for instance).

Embodiments of the present invention would facilitate motivational training and allow for individuals to train together and motivate each other even when they were remote from one another. It is well known that training with a partner can facilitate and enhance the workout through mutual motivation and friendly competition. Embodiments of the present invention provide and allow individuals who are remote from one another to train together. For example, remote individual may share data including physiologic states (pulse, respiration, fatigue etc.) and sporting activity (how fast they are running, biking, etc.). Embodiments of the invention include means for each individual to send user generated feedback to one another such as coaching and encouragement. In some embodiments, virtual reality (VR) or similar technology may be used in order to allow each of the individuals who are sharing data to virtually participate in the environment of the other. For example, an individual on a stationary bike could wear VR goggles that presented a particular simulated/virtual environment that replicates the environment and/or activity of another individual. Wearable devices such as Fit Bit®, apple watches, etc. comprise sensors and other hardware that allows the measurement of certain personal data of the wearer. Additional wearable sensors could also be employed and a computer interface used to calculate and derive specific data about an individual during athletic activity. By sharing this data, individual athletes may compete remotely and may encourage or motivate one another. The shared data may be displayed in real time via a personal device such as a smartphone, smart watch or the like according to some embodiments.

Figure 8:
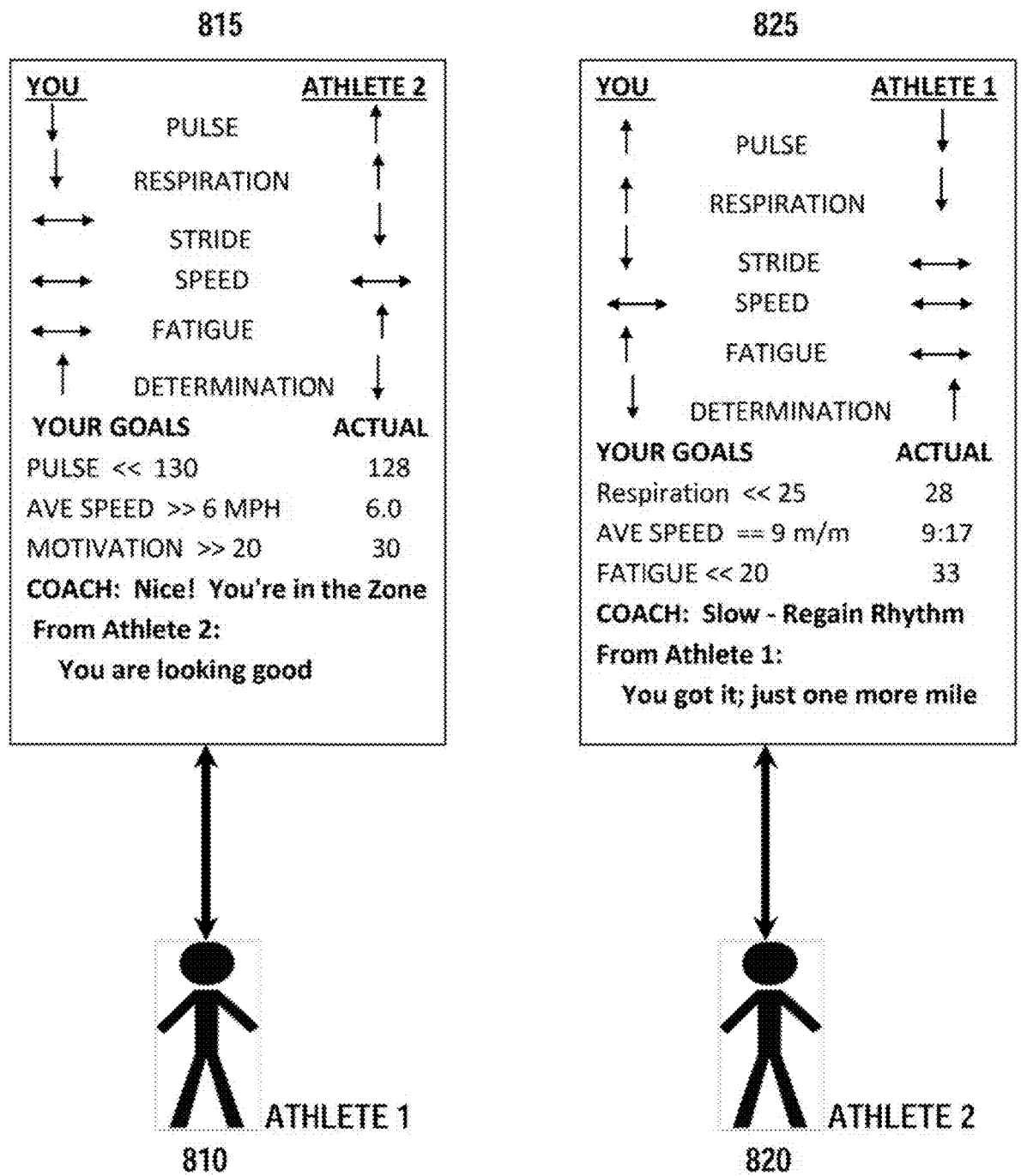
FIG. 8 illustrates example feedback displays for a competitive athletic training system according to some embodiments.

FIG. 8 illustrates example feedback displays for a competitive athletic training system according to some embodiments. Athlete1 810 and Athlete2 820 are equipped with biological and other sensors (not shown) which measure in real time physiological and other athlete data. The sensors are connected (e.g., via wires or wirelessly) to a local computer, e.g., smartphone (not shown), which comprises a processor for processing, communicating and displaying the raw sensor data as well as derived data. In some embodiments the local processor analyzes the data to generate an estimated emotional state or affect for display to the athlete. The data collection for and on each athlete may be synchronized with that of other athletes and the raw and derived data is displayed on the smartphones or other displays carried or viewable by each of the athletes. In some embodiments, communication of data to the athletes is done audibly (e.g., via ear buds); in other embodiments, communication of the data to the athletes is accomplished via tactile mean (wristband or other wearable unit vibrating, pulsing etc.)

In some embodiments, the raw sensor data is communicated to a remote server (not on the person of the athlete) which processes the data and generates derived data, and this data is then communicated back to the athletes for display. 815 and 825 illustrate examples of information that may be displayed or otherwise communicated to the Athlete1 810 and Athlete2 850 respectively. These are examples only and the invention is not limited to any particular data being displayed (or not displayed) or by any means of displaying or otherwise communicating data and/or coaching to the athletes. As shown in FIG. 8, displays 815 and 825 display both raw physiological data and derived data of both athletes. Each athlete sees their own data as well as that of the other athlete (e.g., their training partner). Additionally, a virtual coach, based on the goals set by each athlete and their respective actual performance, can provide feedback to encourage, guide or otherwise help the individual athlete. Each athlete monitors their own performance as well as their training partner(s) and the athletes can provide comments to each other before, during and after the competitive or recreational activity.

While the invention has been described with reference to exemplary embodiments, it will be understood by those skilled in the art that various changes may be made and equivalents may be substituted for elements thereof without departing from the scope of the invention. Furthermore, while the above description contains much specificity, these should not be construed as limitations on the scope of any embodiment, but as exemplifications of the presented embodiments thereof. Many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments that may be contemplated based on the above description. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Furthermore, although a variety of potential system inputs, variables, measurements, processing outputs, and other details have been described, embodiments of the invention are not limited to implementations of any specific number of these parameters, and embodiments of the invention may include a large or minimal set of these parameters depending on the application or desired need. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method of sharing emotional, psychological or affective data or state of an individual with another individual during remote social interaction comprising the steps of:
   providing a software application running on a computer device for social interaction between a first user and a second user wherein said first and second users are remote from each other
   providing means for measuring, estimating or deriving physiological or physical characteristics or responses of said first user wherein said means includes one or more sensors or transducers attached to, connected to or proximate to the first user;
   receiving a subjective impression of the first user's current emotional, psychological or affective state from the first user;
   receiving a first datum related to the first user wherein said first datum is a measured or derived datum representing a current first physiological or physical characteristic or response of said first user;
   generating an estimate of a current emotional, psychological or affective state or change of emotional, psychological or affective state of the first user wherein said estimate is derived using said received first user's subjective impression of said first user's current emotional, psychological or affective state and said received first datum related to the first user and wherein said generating is accomplished via a computing system comprising an adaptive self learning software engine, artificial intelligence, a neural network, a rules based algorithm or look-up table implemented on a computer processor; and
   providing said estimate of current emotional, psychological or affective state or change of emotional, psychological or affective state of the first user to the second user wherein said first user shares the first user's current emotional, psychological or affective state or change thereto with the second user.

2. The method of claim 1 wherein the first user may tune or adjust a parameter of said computing system wherein said first user may, by adjusting said parameter of the computing system, improve accuracy of the estimate of emotional, psychological or affective state or changes thereto of said first user generated by the computing system.

3. The method of claim 2 further comprising the step of: providing said estimate of the current emotional, psychological or affective state of the first user to the first user and prompting said first user to appraise said estimate wherein said prompting requests the first user to provide to the software application the first user's perceived accuracy of the estimate of the first user's current emotional, psychological or affective state and further prompts the first user to select at least one current emotion, psychological characteristic or affect of the first user which the first user perceives as either overrepresented or underrepresented by said estimate of the current emotional, psychological or affective state of the first user.

4. The method of claim 2 further comprising the step of: a prompting of or suggesting to the first user by said software application to tune or adjust a parameter of said computing system allowing the first user to adjust a weighting of said first datum or other datums or said first user's subjective impression of said first user's current emotional, psychological or affective state and wherein a user adjusted weighting is used by the computing system adaptive engine in deriving an estimate of a current emotional, psychological or affective state of the user.

5. The method of claim 4 wherein said prompting of or suggesting to the first user by the software application includes a request of the first user to select at least two different subjectively perceived current emotions, psychological characteristics or affects of the first user and wherein the first user is further requested to assign a relative weighting to each subjectively perceived current emotions, psychological characteristics or affects selected by the first user.

6. The method of claim 1 further comprising the steps of: querying or prompting by the software application of said first user to enter a datum representing said first user's subjective impression of said first user's own personality, emotional, psychological or affective tendencies or inclinations; and receiving a datum representing said first user's subjective impression of said first user's own personality, emotional, psychological or affective tendencies or inclinations from the first user; and generating a baseline estimate of said first user's personality, emotional, psychological or affective tendencies or inclinations wherein said baseline estimate is derived using said received user datum representing said first user's subjective impression of said first user's own personality, emotional, psychological or affective tendencies or inclinations and said first datum of the first user wherein the generating of said baseline estimate is performed by the computing system adaptive software engine.

7. The method of claim 6 further comprising the step of: querying or prompting of the first user to enter known emotional triggers or stressors of said first user and wherein the generating of said baseline estimate is derived using first user entered emotional triggers or stressors and wherein said baseline estimate includes an assessment of said first user's tendency to emotional stability, lability and volatility.

8. The method of claim 1 further comprising the steps of: providing means for measuring, estimating or deriving physiological or physical characteristics or responses of said second user wherein said means includes one or more sensors or transducers attached, connected or proximate to the second user and a computer processor; receiving a first datum from the second user wherein said first datum is a measured or derived datum representing a first physiological or physical characteristic or response of said second user; receiving from the second user a subjective impression of the second user's current emotional, psychological or affective state; generating an estimate of a current emotional, psychological or affective state or change of emotional, psychological or affective state of the second user wherein said estimate is derived using said received second user's subjective impression of said second user's current emotional, psychological or affective state, and said received first datum of the second user and wherein said generating is accomplished via said computing system or another computing system comprising an adaptive self learning software engine, artificial intelligence, a neural network or a rules based algorithm or look-up table implemented on a computer processor; and providing said estimate of the current emotional, psychological or affective state of the second user to the first user wherein said second user shares the second user's emotional, psychological or affective state or change thereto with the first user.

9. The method of claim 8 herein the first user and the second user via said software application are able to select or restrict which emotional, psychological or affective state estimate of the respective user is provided or shared with another user.

10. The method of claim 8 wherein said sharing of emotional, psychological or affective state or change of emotional, psychological or affective state via said software application between the first and second users allows the first and second users to become familiar with one another and may facilitate social intercourse and communication between the first and second users including informing one of the first or second user how the other respective user feels and alert the said first or second user to any emotional, psychological or affective changes in the other respective user.

11. The method of claim 1 wherein said first datum represents a physiological or physical characteristic or response that is one of: voice analysis or facial analysis or typing analysis or keypad or grip pressure analysis.

12. A system for estimating emotional, psychological or affective characteristics of individuals in real time during social interactions and for sharing such characteristics with other individuals during the social interaction comprising: a software application that allows users remote from each other to communicate and socially interact with one another; a first sensor or transducer that measures or from which is derived a datum representing a first physiological or physical response of a user;

a user interface to the software application that allows said user to provide the user's subjective impression of the user's current emotional, psychological or affective state; and a computing system comprising an adaptive self learning software engine, artificial intelligence, a neural network, a rules based algorithm or a look-up table that generates an estimate of a current emotional, psychological or affective state of the user wherein said estimate is derived using said datum representing a physiological or physical response of the user and the user's provided subjective impression of the user's current emotional, psychological or affective state and wherein said software application allows the user to share the estimate of the user's current emotional, psychological or affective state with another user during a social interaction with the another user.

13. The system of claim 12 wherein said computing system uses a weighted algorithm and wherein the system operates to allow the user to tune or adjust a parameter of the computing system allowing the user to adjust a weighting of said datum or other datums or said user's subjective impression of said estimate of the user's emotional, psychological or affective state wherein the computing system operates to generate a new estimate of the user's emotional, psychological or affective state based on the tuning or adjusting by the user.

14. The system of claim 12 wherein said first sensor or transducer is a microphone or camera and wherein said datum represents voice analysis or facial analysis of the user and wherein a second sensor or transducer operates to detect salinity or pressure from which a second datum is derived and wherein said second datum represents skin salinity or keypad or grip analysis or muscle tension of the user.

15. The system of claim 12 further comprising:
a group emotion estimator that provides an estimate of a dominant or commonly shared emotion among members of a group of users, said group comprising a plurality of users, each of whom is sharing an emotional, psychological or affective state with other users, wherein said group emotion estimator is implemented via the computing system wherein said computing system applies a weighting to the emotional, psychological or affective states of members of the group to estimate a group emotion.

16. The system of claim 12 further comprising:
an empathy trainer wherein users share emotional or other data and engage in real time meditation, dialog or therapy or other interaction while each user has knowledge of the respective user's own real time emotional, psychological or other data and real time emotional, psychological or other data of another user.

17. A system for sharing emotional, psychological or affective data or states of an individual with another individual in real time during remote social interaction by allowing individuals to share their emotional, psychological or affective states comprising:
a software application running on one or more computing devices allowing social interaction between a first user and a second user wherein said users are remote from one another wherein said
software application allows the first user to provide said first user's subjective impression of the first user's current emotional, psychological or affective state;
means for estimating an emotional, psychological or affective state or change of emotional, psychological or affective state of the first user wherein said means includes one or more sensors or transducers attached, connected or proximal to said first user wherein measured or derived data from said one or more sensors or transducers represent a physiological or physical characteristic or response of the first user and wherein said means for estimating an emotional, psychological or affective state of the first user includes a computing system comprising an adaptive self learning software engine, artificial intelligence, a neural network or a rules based algorithm or look-up table that derives an estimate of emotional, psychological or affective state of the first user using physiological or physical characteristics or responses of the first user wherein said software application allowing social interaction enables the first user to share an emotional, psychological or affective state or change of emotional, psychological or affective state of the first user with the second user;

a personality or affective state baseline estimator that generates a baseline estimate of said first user's personality, emotional, psychological or affective state or inclination wherein said first user's subjective impression of the first user's emotional, psychological or affective state and said first user's physical or physiological response is used by the computing system for generating said baseline estimate;

wherein the software application allows said first user to select or restrict which emotional, psychological or affective state data of the first user is provided to the second user and enables either the first user or the second user to set an alert for a specific emotional, psychological or affective state or change of state of the first user whereby said either first or second user is alerted by the software application if a specific emotional, psychological or affective or change of state of the first user is detected by the application.

18. The system of claim 17 that allows for an application of physical or psychological stimulus to the first user in order to estimate, assess or baseline said first user's personality or emotional inclinations or volatility further comprising:
a human interface attached, connected or proximal to said first user a by which a physical or psychological stimulus is provided to said first user in order to generate a physical or physiological or emotive response of the first user and wherein said physical or physiological or emotive response of the first user is used by the computing system to estimate an emotional or affective state or change of emotional or affective state of the first user or to generate a baseline estimate of said first user's personality, emotional, psychological or affective state or inclination.

19. The system of claim 18
wherein said software application enables the second user to direct, program, or operate said human interface to provide a physical or psychological stimulus to the first user.

20. The system of claim 17
wherein said software application allows for recording real time estimates of emotional, psychological or affective states or changes thereto of the first user over an extended period; and a user interface to said software application allowing the first user or another user to enter specific data regarding the first user's experiences or stimulus during said extended period and that correlates a time evolution of said first user's emotional, psychological or affective states or changes thereto during the extended period with experiences or stimulus encountered by the user during said extended period.

* * * * *